United States Patent
Norman et al.

(10) Patent No.: US 11,135,378 B2
(45) Date of Patent: Oct. 5, 2021

(54) FLUID WARMING TUBE AND CONNECTOR

(71) Applicant: Neonatal Product Group, Inc., Stilwell, KS (US)

(72) Inventors: Scott Norman, Stilwell, KS (US); Mark Petheram, Overland Park, KS (US)

(73) Assignee: Neonatal Product Group, Inc., Stilwell, KS (US)

( * ) Notice: Subject to any disclaimer, the term of this patent is extended or adjusted under 35 U.S.C. 154(b) by 61 days.

(21) Appl. No.: 16/392,941

(22) Filed: Apr. 24, 2019

(65) Prior Publication Data
US 2020/0338280 A1 Oct. 29, 2020

(51) Int. Cl.
*A61M 5/44* (2006.01)
*A61M 39/10* (2006.01)
*A61J 1/10* (2006.01)

(52) U.S. Cl.
CPC ............... *A61M 5/445* (2013.01); *A61J 1/10* (2013.01); *A61M 39/10* (2013.01); *A61M 2039/1022* (2013.01); *A61M 2039/1038* (2013.01); *A61M 2205/0233* (2013.01); *A61M 2205/3368* (2013.01); *A61M 2205/3653* (2013.01)

(58) Field of Classification Search
CPC ........ A61M 5/445; A61M 5/44; A61M 39/10; A61M 2205/338; A61B 18/08; A61B 18/12; A61B 2018/00636; A61B 2018/00714; A61B 2018/00791

USPC ......................................................... 604/114
See application file for complete search history.

(56) References Cited

U.S. PATENT DOCUMENTS

| | | | | |
|---|---|---|---|---|
| 4,176,660 A | * | 12/1979 | Mylrea | A61B 5/285 600/484 |
| 9,814,845 B1 | * | 11/2017 | Norman | A61J 15/00 |
| 2009/0319011 A1 | * | 12/2009 | Rosiello | F24H 1/142 607/105 |
| 2010/0280454 A1 | * | 11/2010 | Rosiello | A61M 5/44 604/114 |

* cited by examiner

*Primary Examiner* — Nathan R Price
*Assistant Examiner* — John A Doubrava
(74) *Attorney, Agent, or Firm* — Hovey Williams LLP

(57) ABSTRACT

A tube and connector assembly for warming an intravenous fluid comprises a tube, a temperature sensor, and a connector. The tube includes a single hollow generally cylindrical side wall with an inner surface along which the intravenous fluid flows. The tube further includes first and second electrically conductive wires, each within the side wall and electrically connected to one another to carry electrical current to warm the intravenous fluid. The temperature sensor is configured to measure a temperature of the fluid flowing through the tube. The connector includes first, second, and third side walls. The first side wall receives the tube. The second side wall is positioned opposite the first side wall and is configured to receive line tubing. The third side wall is spaced apart from the second side wall and includes threads on an inner surface thereof configured to receive a line connector for the intravenous line.

5 Claims, 13 Drawing Sheets

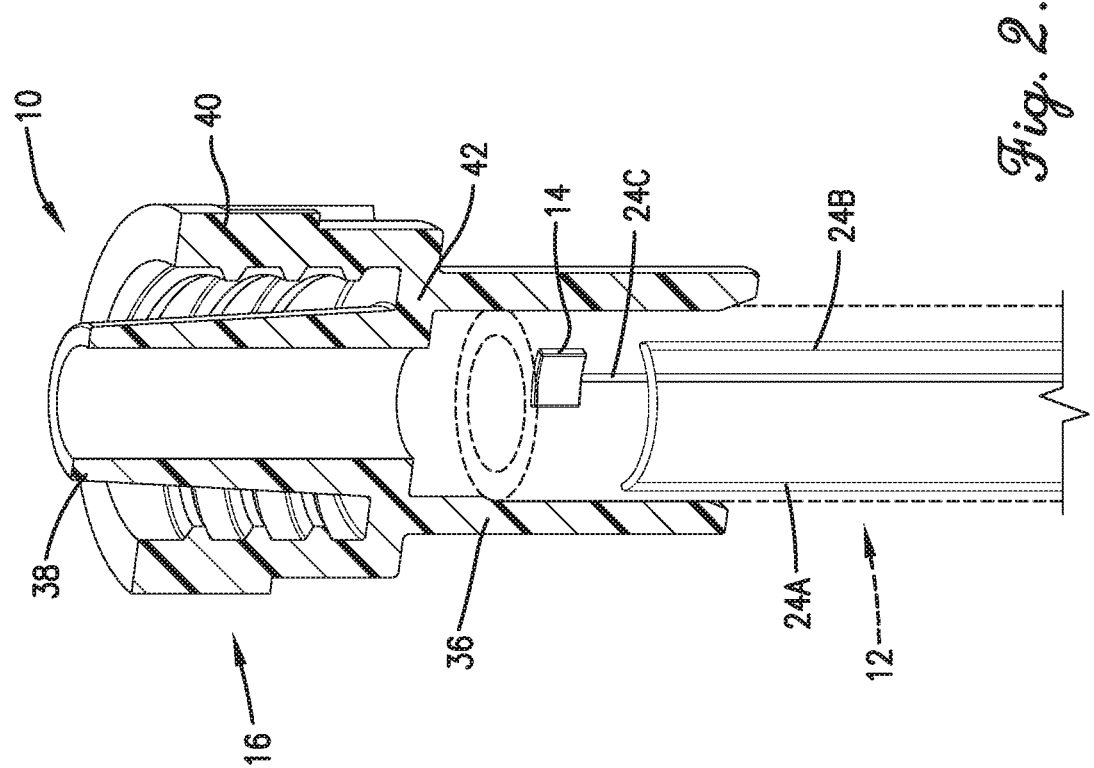
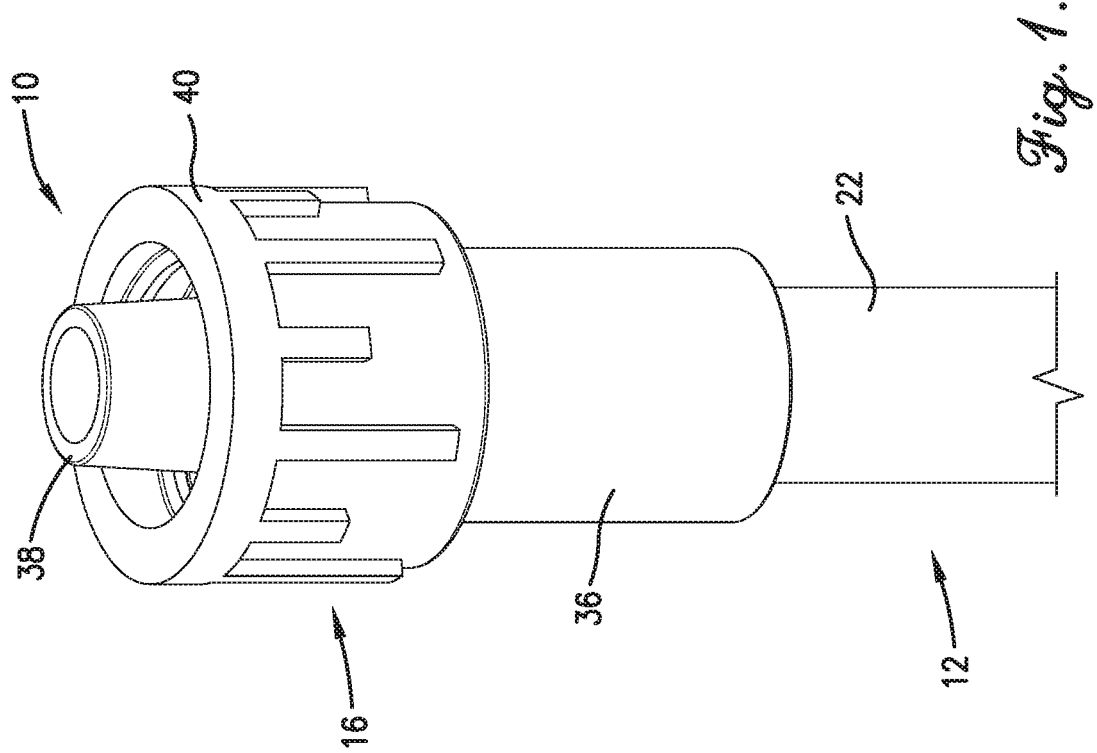

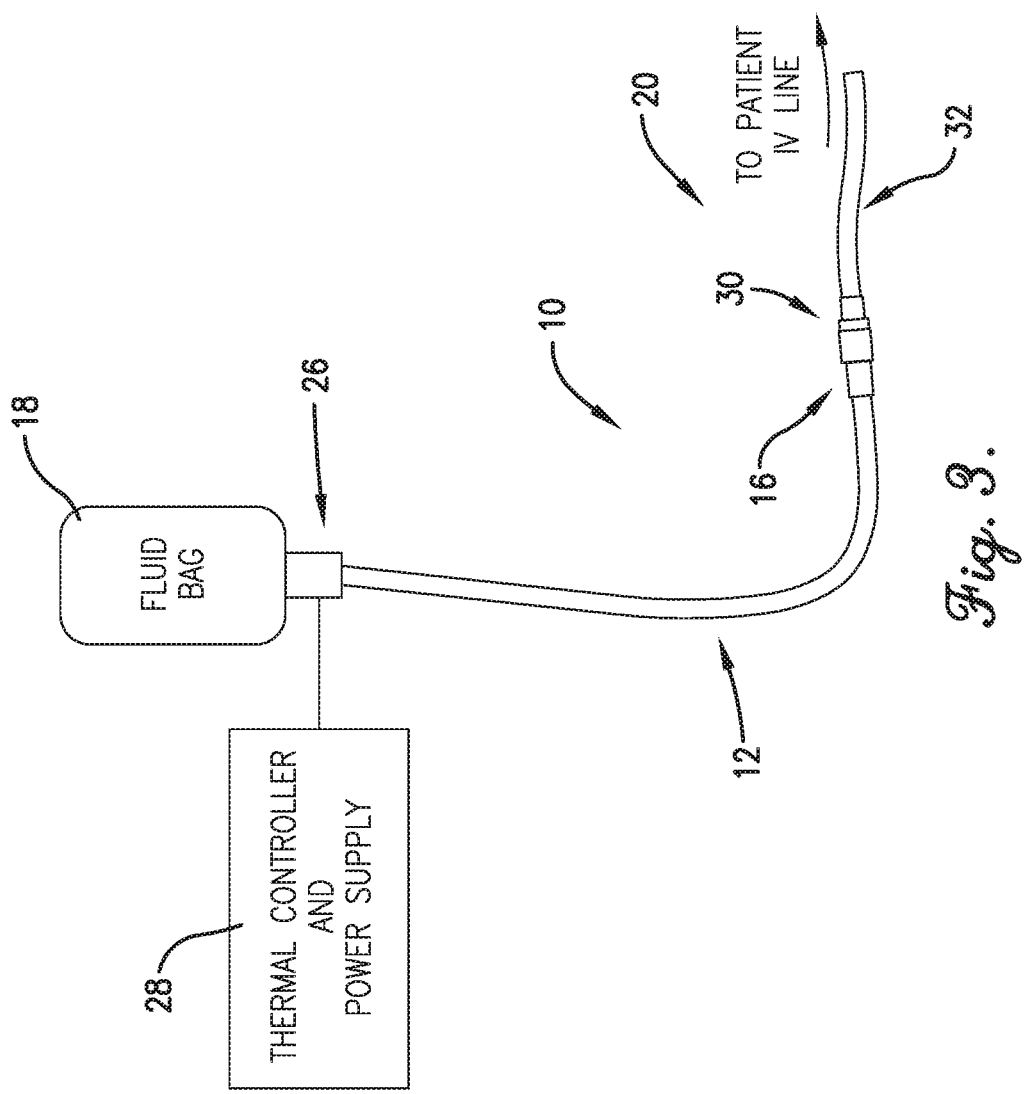

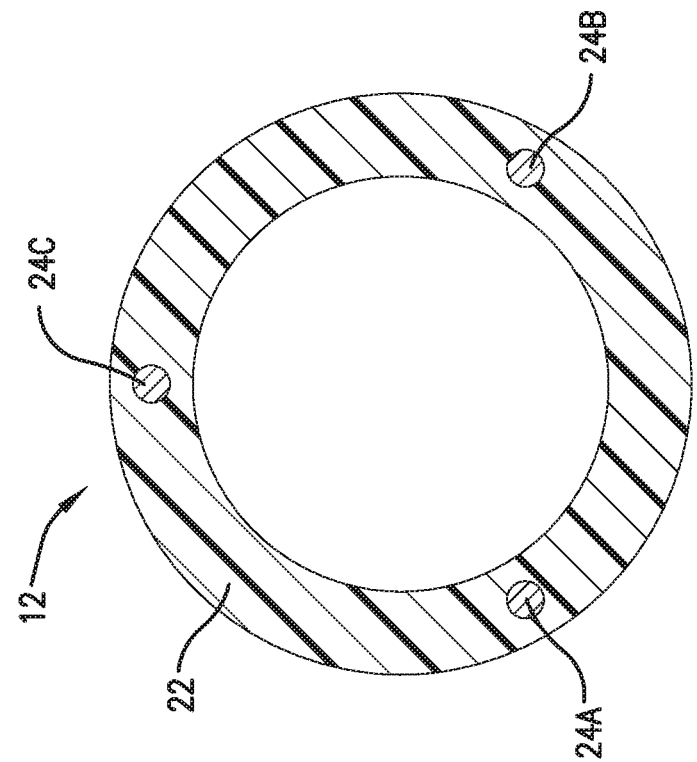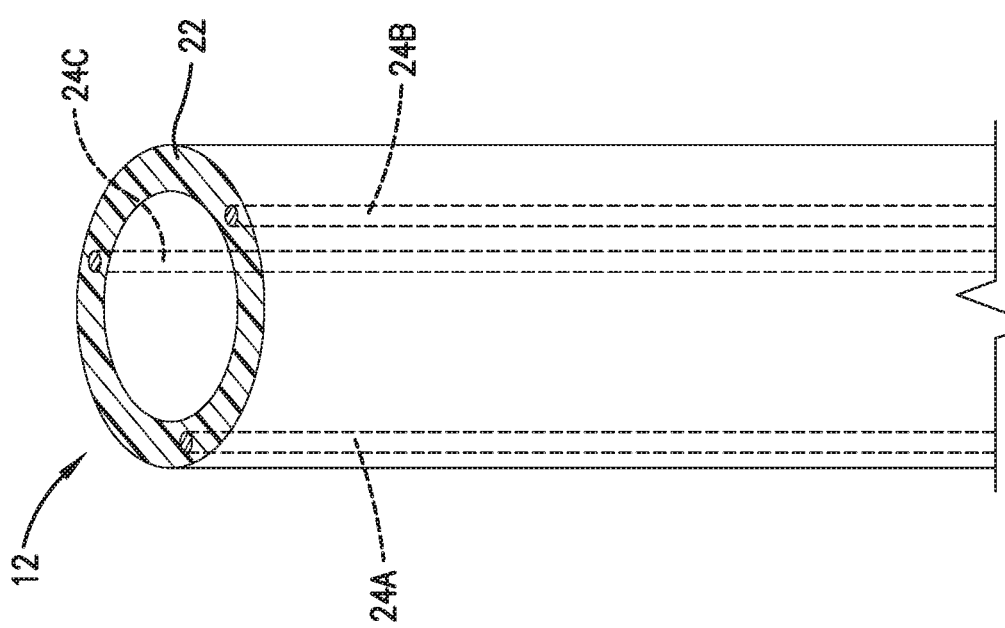

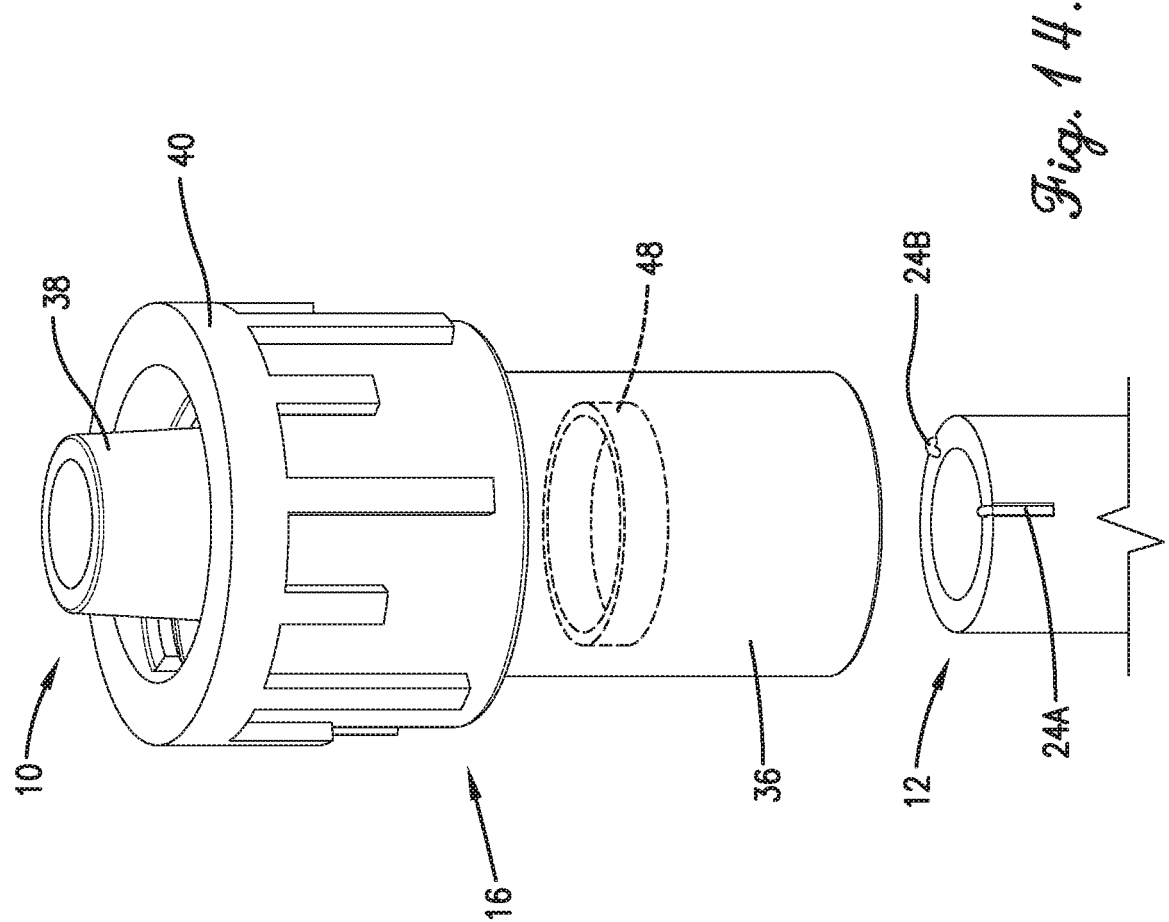

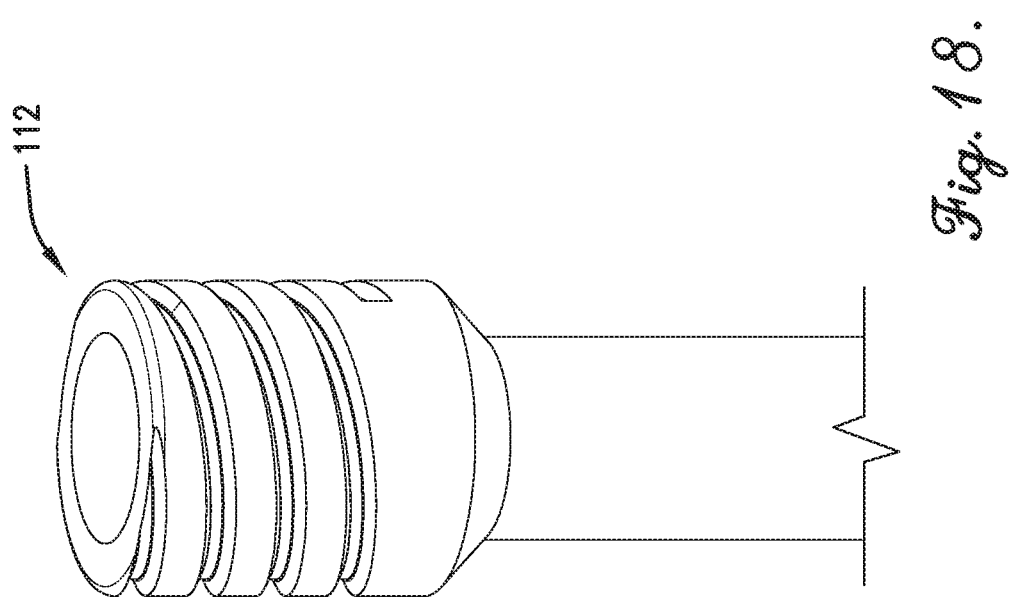
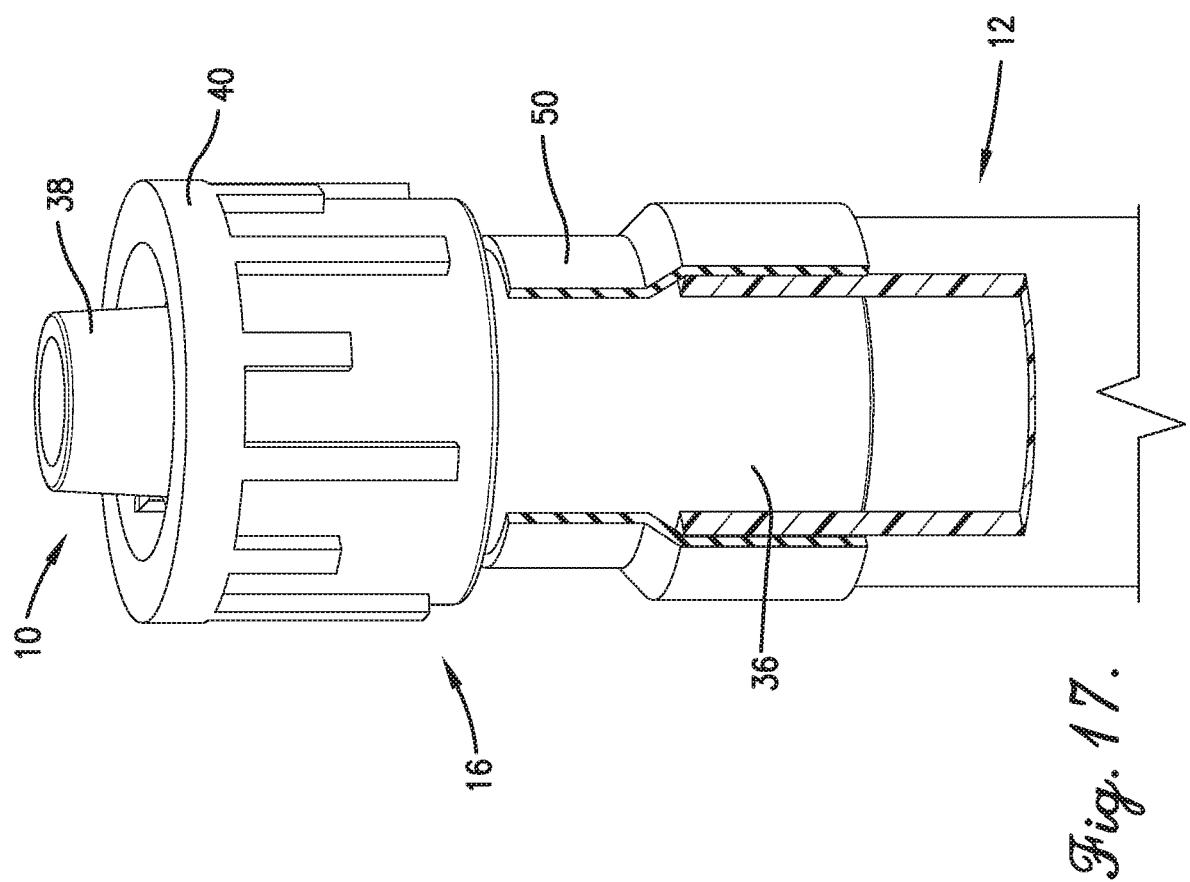

FLUID WARMING TUBE AND CONNECTOR

FIELD OF THE INVENTION

Embodiments of the current invention relate to a tube and connector assembly for warming fluid to be used in medical procedures.

DESCRIPTION OF THE RELATED ART

Intravenous fluid, such as saline solution, blood, and other fluid, is typically supplied from a bag that is hung from an elevated hanger in proximity to a patient. The fluid is delivered through a first tube that connects to the bag and terminates with a connector. A second tube delivers the fluid to an intravenous needle that enters the patient's body. The second tube is connected to the first tube through the connector. Often, the bag is stored in a cold environment to preserve properties of the fluid. Although the bag may be warmed before use with a patient, the fluid may not heat up adequately before being supplied to the intravenous needle causing patient discomfort.

SUMMARY OF THE INVENTION

Embodiments of the current invention solve the above-mentioned problems and provide a tube and connector assembly capable of heating intravenous fluid by heating the tube that connects to the intravenous fluid supply bag. The assembly is also capable of monitoring a temperature of the fluid as it passes through the connector in order to warm the fluid to a desired temperature before it leaves the assembly. The tube and connector assembly comprises a tube, a temperature sensor, and a connector. The tube includes a single hollow generally cylindrical side wall with an outer surface and an inner surface along which the intravenous fluid flows. The tube further includes a first electrically conductive wire and a second electrically conductive wire with each wire being retained along an axial length within the side wall. The first and second wires are electrically connected to one another near one end of the tube and are configured to carry electrical current to warm the intravenous fluid. The temperature sensor is configured to measure a temperature of the fluid flowing through the tube. The connector is configured to couple to the tube and includes a first side wall, a second side wall, and a third side wall, each of which has a hollow generally cylindrical shape. The first side wall is configured to receive the tube. The second side wall is positioned opposite the first side wall and is configured to receive line tubing from an intravenous line. The third side wall is spaced apart from and concentric with the second side wall. The third side wall includes threads on an inner surface thereof and is configured to receive a line connector for the intravenous line.

Another embodiment of the current invention provides a tube and connector assembly for warming an intravenous fluid. The assembly comprises a tube, a temperature sensor, and a connector. The tube includes a single hollow generally cylindrical side wall with an outer surface and an inner surface along which the intravenous fluid flows. The tube further includes a first electrically conductive wire, a second electrically conductive wire, and a third electrically conductive wire, each retained along an axial length within the side wall. The first and second wires extend beyond the end of the tube and are in physical contact with one another to form an electrical connection. The first and second wires are configured to carry electrical current to warm the tube and the intravenous fluid. The temperature sensor is positioned within the side wall of the tube and is electrically connected to the third wire. The temperature sensor is configured to measure a temperature of the fluid flowing through the tube. The connector is configured to couple to the tube and includes a first side wall, a second side wall, and a third side wall, each of which has a hollow generally cylindrical shape. The first side wall is configured to receive the tube. The second side wall is positioned opposite the first side wall and is configured to receive line tubing from an intravenous line. The third side wall is spaced apart from and concentric with the second side wall. The third side wall includes threads on an inner surface thereof and is configured to receive a line connector for the intravenous line.

Yet another embodiment of the current invention provides a tube and connector assembly for warming an intravenous fluid. The assembly comprises a tube, a temperature sensor, and a connector. The tube includes a single hollow generally cylindrical side wall with an outer surface retaining threads thereon and an inner surface along which the intravenous fluid flows. The tube further includes a first electrically conductive wire and a second electrically conductive wire with each wire being retained along an axial length within the side wall. The first and second wires are electrically connected to one another near one end of the tube and are configured to carry electrical current to warm the intravenous fluid. The temperature sensor is configured to measure a temperature of the fluid flowing through the tube. The connector is configured to couple to the tube and includes a first side wall, a second side wall, and a third side wall, each of which has a hollow generally cylindrical shape. The first side wall has a first end configured to receive the tube and an opposing second end configured to receive line tubing from an intravenous line. The second side wall is spaced apart from and concentric with the first end of the first side wall. The second side wall includes threads on an inner surface thereof and is configured to receive the threads on the tube. The third side wall is spaced apart from and concentric with the second end of the first side wall. The third side wall includes threads on an inner surface thereof and is configured to receive a line connector for the intravenous line.

BRIEF DESCRIPTION OF THE DRAWING FIGURES

Embodiments of the current invention are described in detail below with reference to the attached drawing figures, wherein:

FIG. 1 is a perspective view of a tube and connector assembly for warming an intravenous fluid, constructed in accordance with various embodiments of the current invention, the assembly comprising a tube, a temperature sensor, and a connector;

FIG. 2 is a perspective view of the assembly of FIG. 1 with a sectional view of the connector and a transparent view of the tube to illustrate the temperature sensor and a plurality of wires retained within the tube;

FIG. 3 is an environmental view depicting the tube and connector assembly in usage with an intravenous fluid bag and a patient intravenous line;

FIG. 4 is a perspective view of a section of the tube cut transverse to the longitudinal axis which additionally illustrates the wires retained within the tube;

FIG. 5 is a top view of the section of the tube of FIG. 4 highlighting the wires within the tube;

Figure 11:
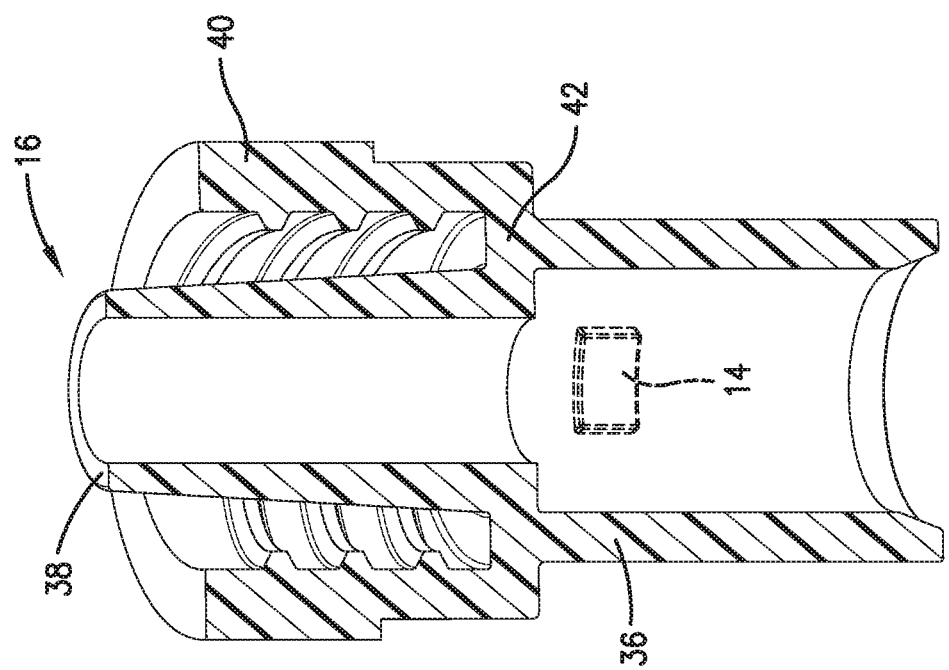
Figure 13:
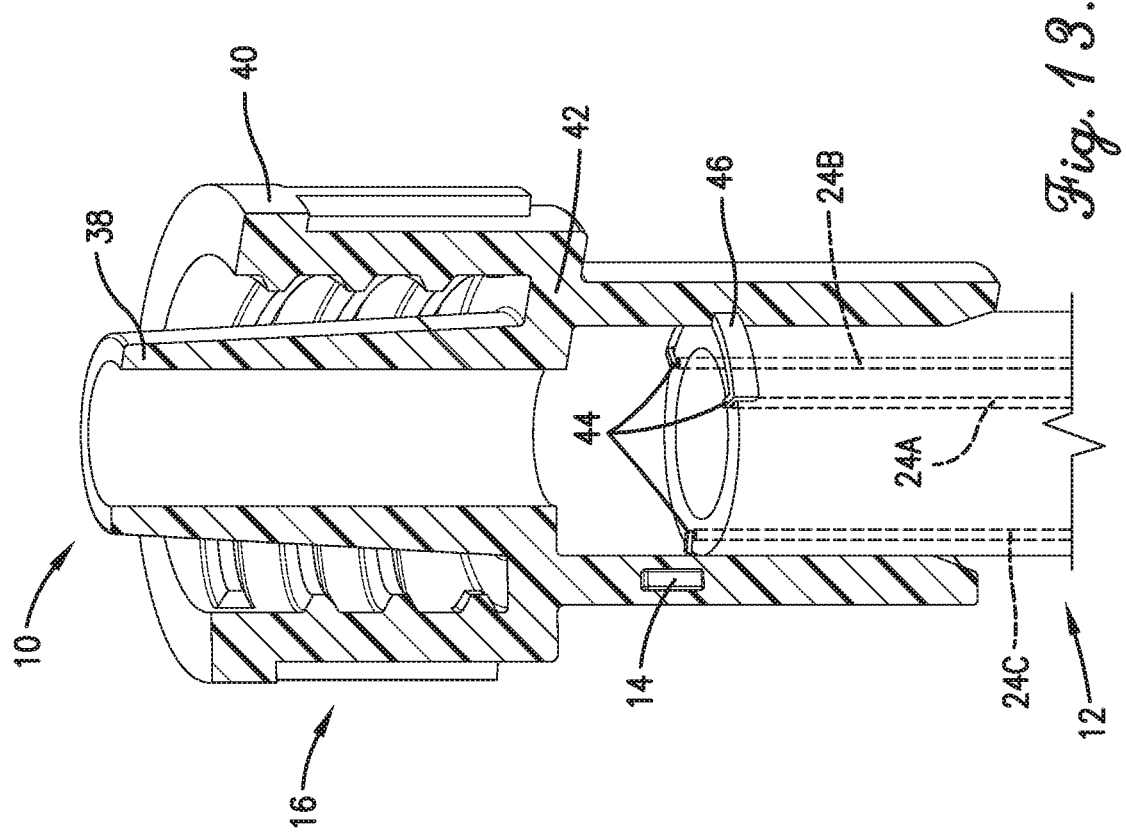
Figure 12:
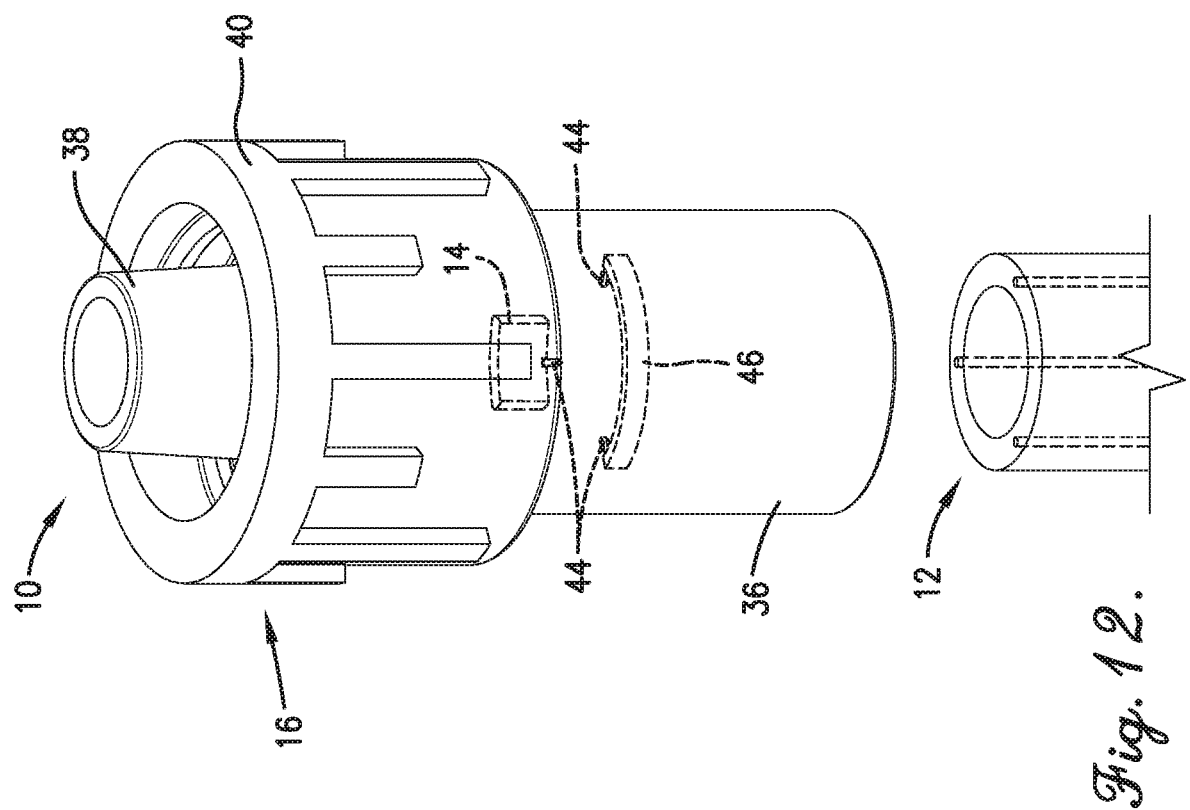
Figure 16:
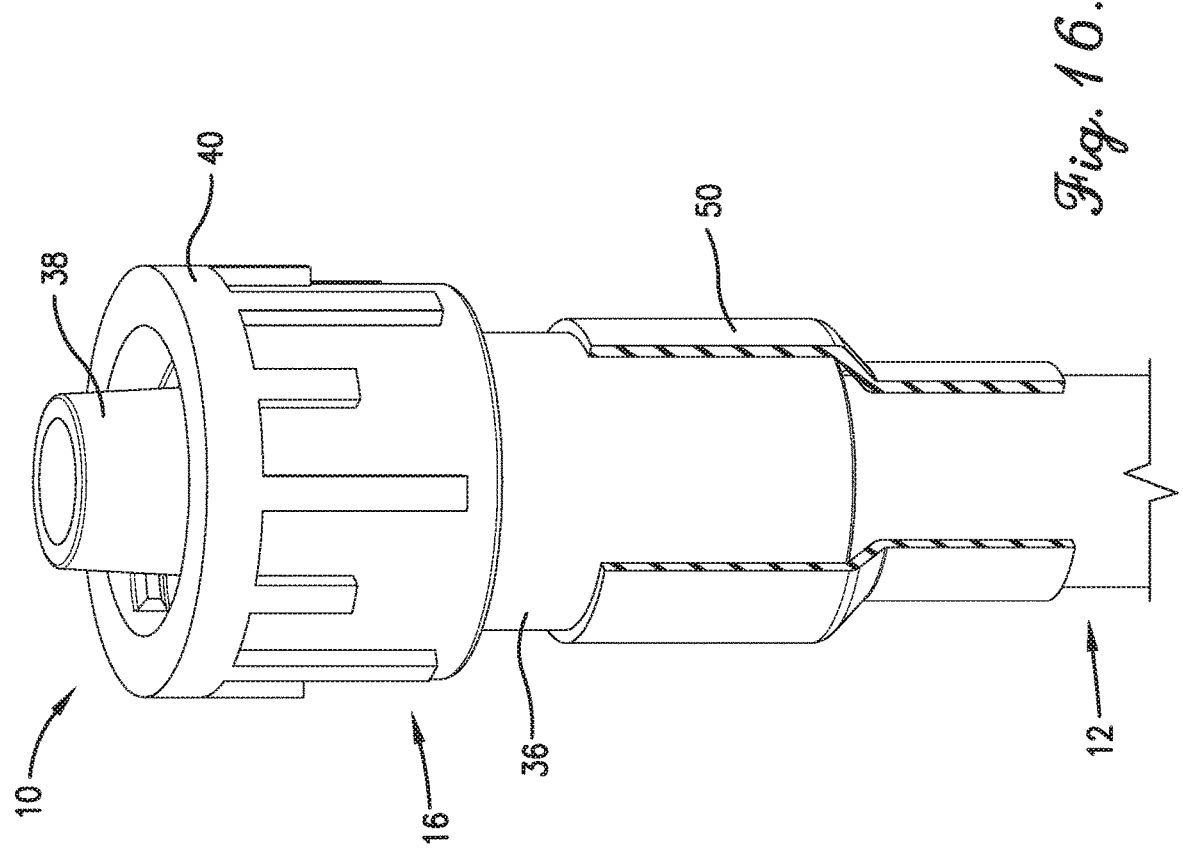
Figure 15:
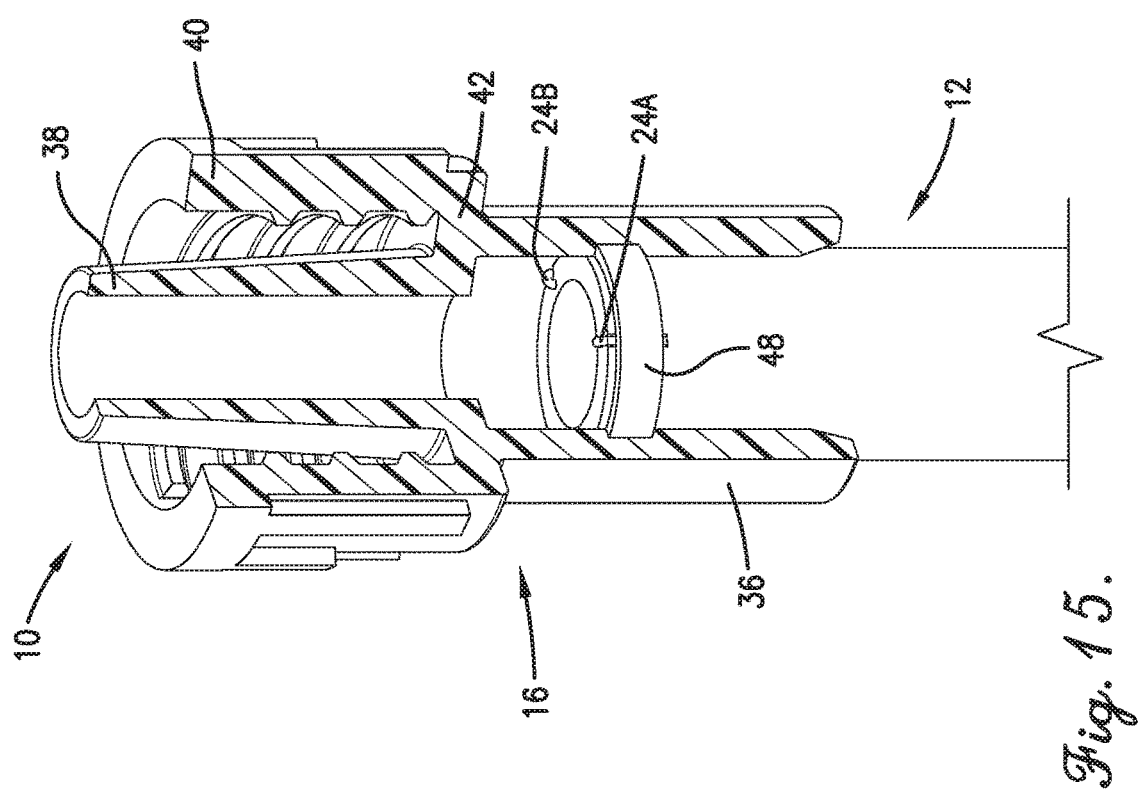
Figure 20:
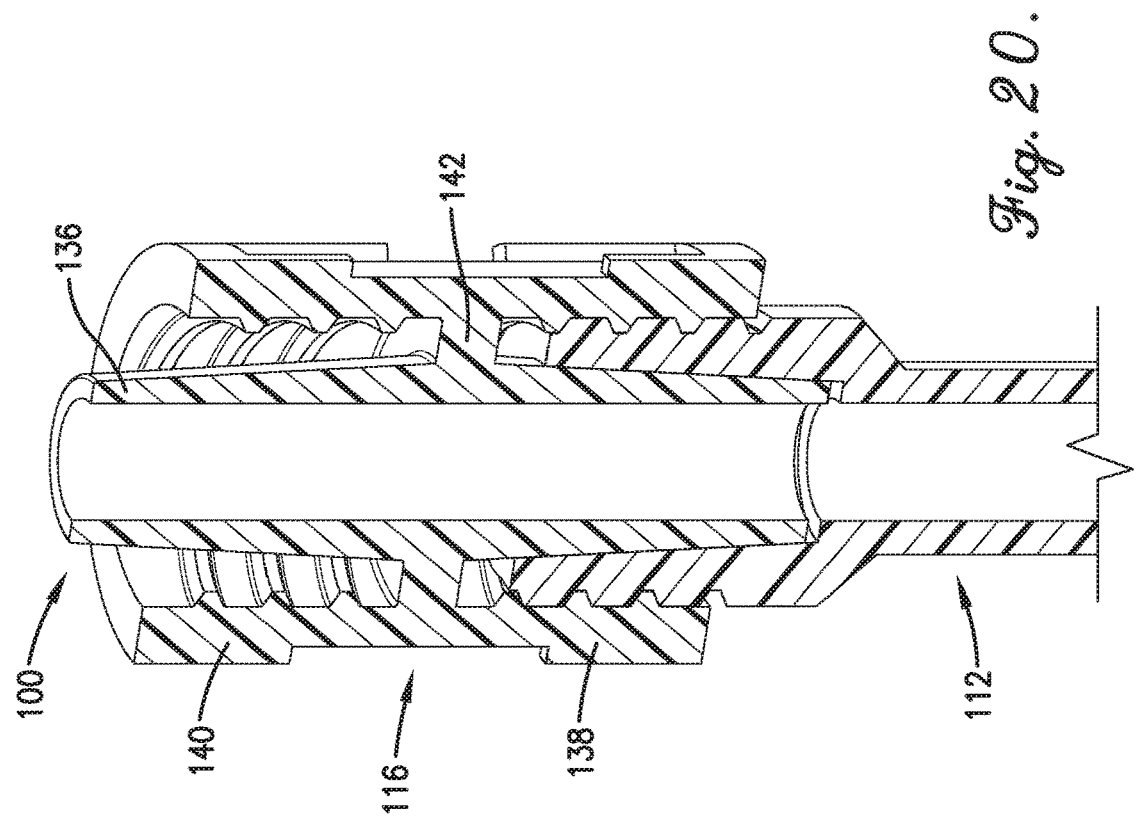
Figure 19:
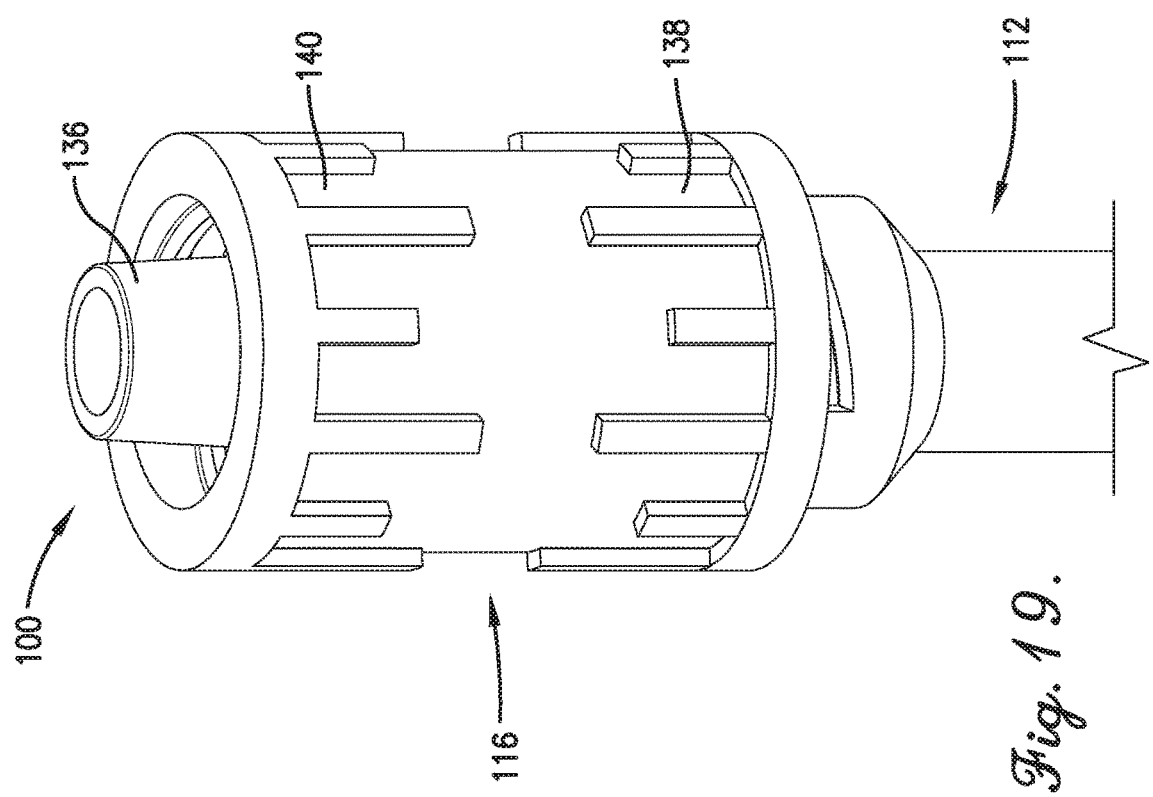
Figure 22:
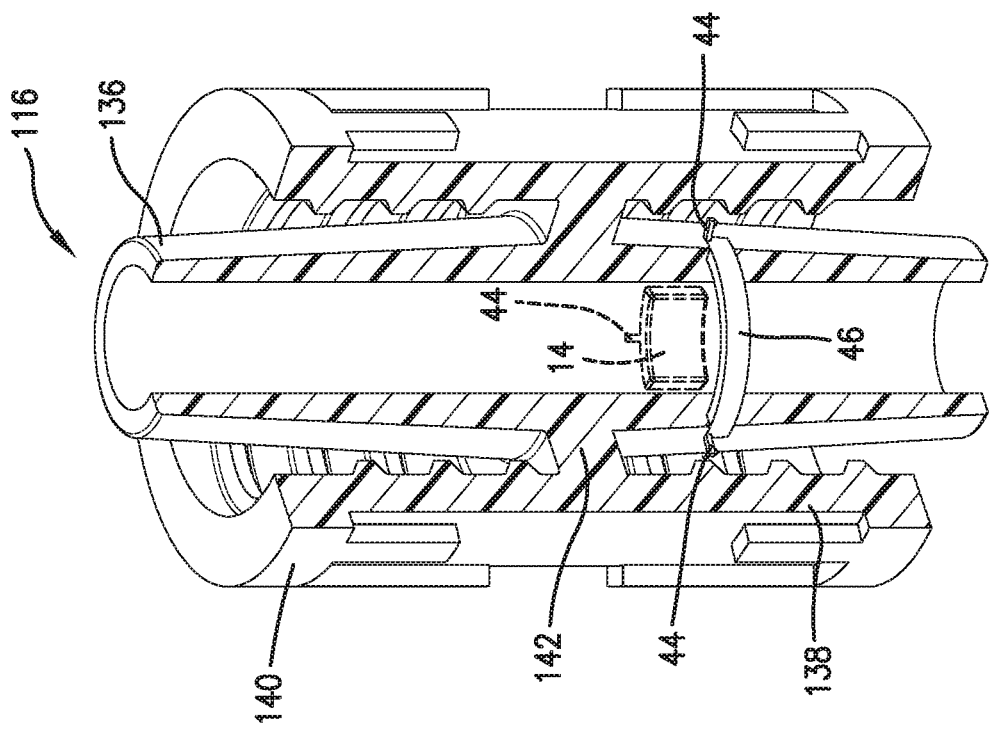
Figure 21:
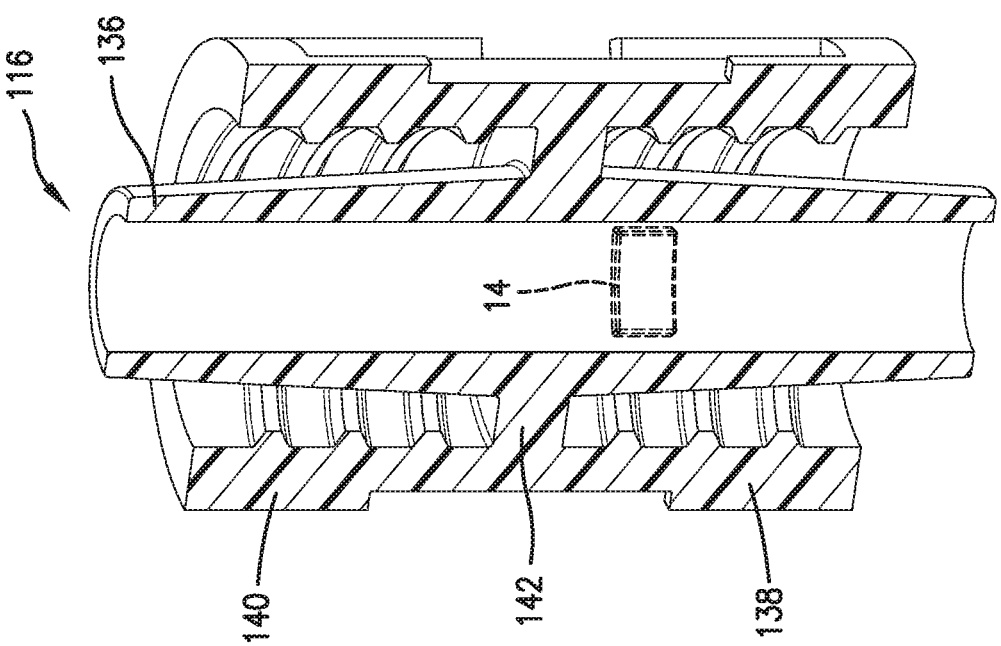
Figure 24:
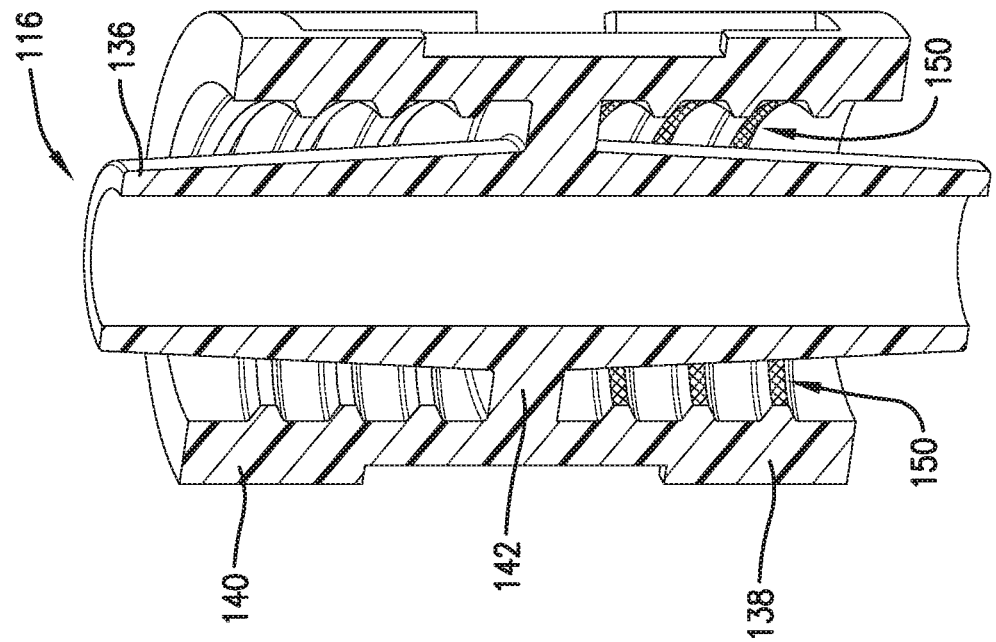
Figure 23:
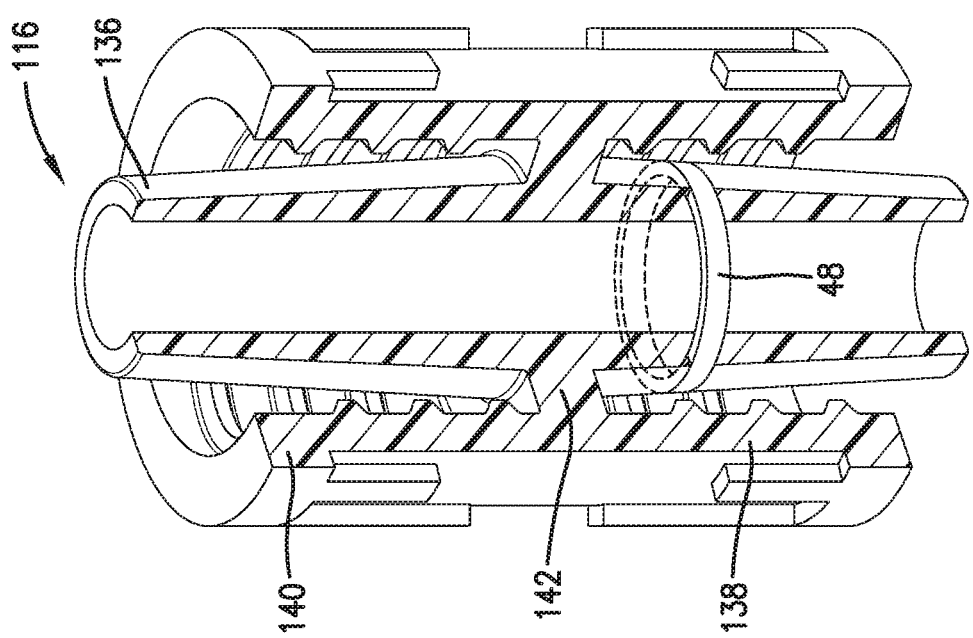

FIG. 11 a perspective cross-sectional view of the connector cut along a longitudinal axis illustrating the temperature sensor being positioned within a side wall of the connector;

FIG. 12 is a perspective view of the tube separated from the connector with one configuration of the connector that includes a plurality of jumpers retained within the side wall;

FIG. 13 is a perspective view of the tube coupled to the connector with a sectional view of the connector illustrating that the jumpers make contact with the wires of the tube;

FIG. 14 is a perspective view of the tube separated from the connector with another configuration of the connector that includes an electrically conductive ring retained in the side wall of the connector;

FIG. 15 is a perspective view of the tube coupled to the connector with a sectional view of the connector illustrating that the ring makes contact with the wires of the tube;

FIG. 16 is a perspective view of the tube and connector assembly further comprising a sleeve that covers a joint of the tube and connector, wherein the tube is positioned inside the connector;

FIG. 17 is a perspective view of the tube and connector assembly including the sleeve covering the joint of the tube and connector, wherein the connector is positioned inside the tube;

FIG. 18 is a perspective view of a second embodiment of the tube including threads on an outer surface of one end of the tube;

FIG. 19 is a perspective view of a second embodiment of the assembly with the second embodiment of the tube coupled to a second embodiment of the connector;

FIG. 20 is a perspective cross-sectional view of the second embodiment of the assembly illustrating the threaded end of the tube engaging with a threaded end of the connector;

FIG. 21 is a perspective cross-sectional view of the second embodiment of the connector including the temperature sensor retained within a first side wall of the connector;

FIG. 22 is a perspective cross-sectional view of the second embodiment of the connector including the first, second, and third jumpers retained within the first side wall;

FIG. 23 is a perspective cross-sectional view of the second embodiment of the connector including the electrically conductive ring retained within the first side wall; and FIG. 24 is a perspective cross-sectional view of the second embodiment of the connector including an electrically conductive material embedded in, or an electrically conductive coating applied to, internal threads of a second side wall of the connector.

The drawing figures do not limit the current invention to the specific embodiments disclosed and described herein.

The drawings are not necessarily to scale, emphasis instead being placed upon clearly illustrating the principles of the invention.

DETAILED DESCRIPTION OF THE EMBODIMENTS

The following detailed description of the technology references the accompanying drawings that illustrate specific embodiments in which the technology can be practiced. The embodiments are intended to describe aspects of the technology in sufficient detail to enable those skilled in the art to practice the technology. Other embodiments can be utilized and changes can be made without departing from the scope of the current invention. The following detailed description is, therefore, not to be taken in a limiting sense. The scope of the current invention is defined only by the appended claims, along with the full scope of equivalents to which such claims are entitled.

A fluid warming tube and connector assembly 10, constructed in accordance with various embodiments of the current invention, is shown in FIGS. 1-17. The tube and connector assembly 10 broadly comprises a tube 12, a temperature sensor 14, and a connector 16. The tube and connector assembly 10 may be utilized to warm a fluid such as an intravenous (IV) hydration fluid, blood, or other fluids or solutions and may interface with a fluid bag 18 and an IV line 20, as described more detail below.

The tube 12, as shown in FIGS. 1-10 and 12-17, has a generally hollow cylindrical shape with a single circumferential side wall 22, presenting an outer surface and an inner surface, along which the fluid flows. The tube 12 is formed from flexible, optionally resilient, material such as polymers, rubbers, or combinations thereof, which allow the tube 12 to bend or flex freely.

The tube 12 retains a plurality of electrically conductive wires 24 within the side wall 22. Each wire 24 is formed from a metal such as copper, aluminum, or the like, or alloys thereof. The wires 24 includes at least a first wire 24A and a second wire 24B, which carry electrical current. The first and second wires 24A, 24B are joined together, or electrically connected to one another, at one end of the tube 12. In some embodiments shown in FIGS. 2, 6, and 7, the first and second wires 24A, 24B are a single wire that forms a loop, or an inverted U-shape, within the side wall 22 of the tube 12. In other embodiments shown in FIG. 8, the first and second wires 24A, 24B extend from the end of the tube 12 and are tied together to form an electrical connection. Alternatively, the first and second wires 24A, 24B extend from the end of the tube 12 and are soldered together. In still other embodiments shown in FIGS. 9 and 10, each of the first and second wires 24A, 24B terminates within the side wall 22, but are electrically connected by electrically conductive paste deposited in a channel in the side wall 22 between the first and second wires 24A, 24B. The paste and the channel may be covered by electrically insulating material.

Otherwise, the first and second wires 24A, 24B are spaced apart from one another along the circumference of the side wall 22. In addition, the first and second wires 24A, 24B extend along the axial length of the tube 12 in a straight line fashion, in a helical fashion, or the like. The wires 24 may include a third wire 24C which electrically connects to the temperature sensor 14 when a wired temperature sensor is utilized. The third wire 24C is positioned along the circumference of the side wall 22 between the first and second wires 24A, 24B. As with the first and second wires 24A, 24B, the third wire 24C may extend along the axial length of the tube 12 in a straight line fashion, in a helical fashion, or the like.

The tube 12 has a first end and an opposing second end. The first end is configured to couple to the connector 16, as shown in FIGS. 1, 2, and 12-17. The second end couples to a fluid bag connector 26, as shown in FIG. 3. The fluid bag connector 26 includes a fluid port which couples to the fluid bag 18 and receives the fluid that flows through the tube 12. The fluid bag connector 26 also couples to a thermal controller and power supply 28 which supplies electric voltage and/or electric current to the first and second wires 24A, 24B. The thermal controller and power supply 28 also receives thermal or temperature information from the temperature sensor 14 and adjusts the electric voltage and/or electric current to the first and second wires 24A, 24B in order to maintain a desired temperature of the fluid. The fluid bag connector 26 may include an electrical port or receptacle which receives a plug from the thermal controller and power supply 28. The plug may provide the electric voltage and/or electric current. Alternatively, the fluid bag connector 26 may include a cable comprising the wires 24 from the tube 12. The cable may include a plug that couples with the thermal controller and power supply 28 which receives the electric voltage and/or electric current.

The temperature sensor 14 generally senses or measures the temperature of the fluid within the tube 12 and outputs a temperature signal that includes an electrical characteristic, such as an electrical voltage, an electrical current, an electrical resistance, or the like, which varies according to the temperature being sensed. In other embodiments, the temperature sensor 14 may output digital temperature data which varies according to the temperature being sensed. The temperature sensor 14 may include temperature sensing components such as thermocouples, thin-film sensors, resistance temperature detectors, thermistors, or the like, or combinations thereof. In some embodiments, the temperature sensor 14 may communicate the temperature signal or data through an electrically-conductive wire. In other embodiments, the temperature sensor 14 may include radio-frequency (RF) wireless transmitters, and optional receivers, which communicate the temperature data wirelessly.

The tube 12 may be implemented in one of several configurations as shown in the figures and described as follows. In a first configuration shown in FIGS. 2 and 6, the tube 12 includes the first and second wires 24A, 24B electrically connected to one another near the first end. The tube 12 includes the third wire 24C electrically connected to the temperature sensor 14, which is positioned near the first end.

Figure 6:
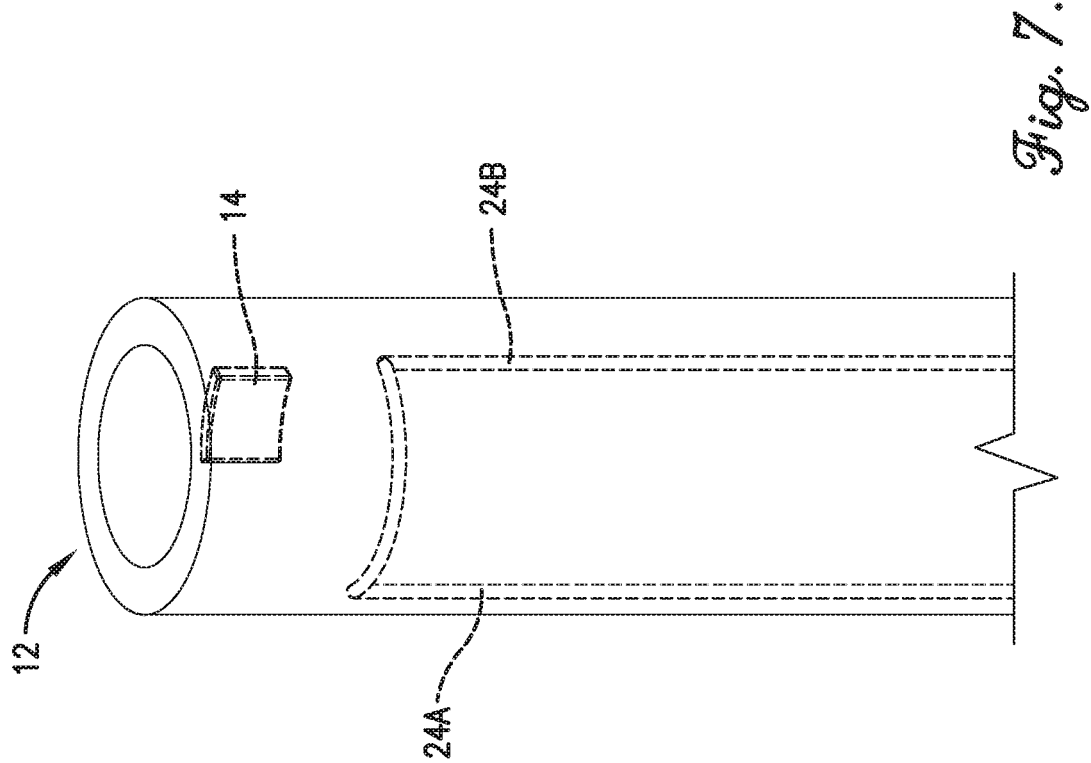
FIG. 6 is a perspective view of one configuration of the tube with a wired temperature sensor.
Figure 7:
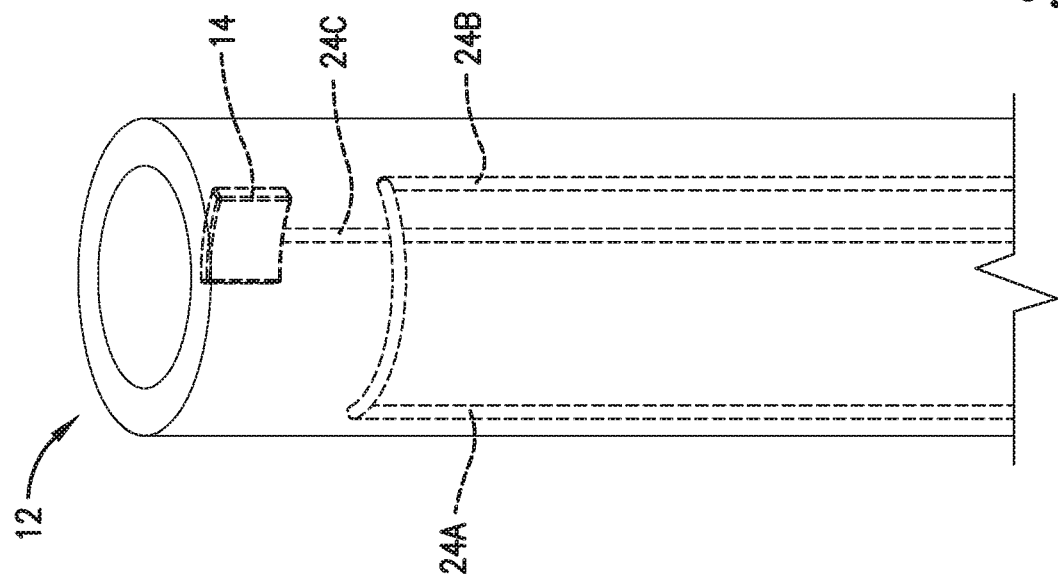
FIG. 7 is a perspective view of another configuration of the tube with a wireless temperature sensor.

In a second configuration shown in FIG. 7, the tube 12 includes the first and second wires 24A, 24B as implemented in the first configuration. But, the second configuration includes a wireless temperature sensor 14 and thus, does not include the third wire 24C.

Figure 8:
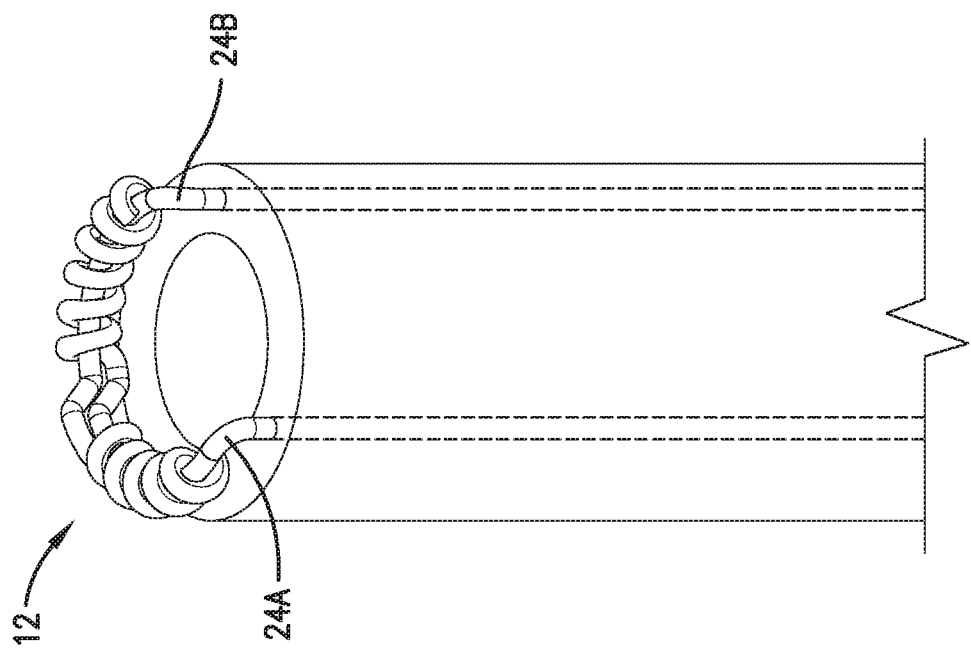
FIG. 8 is a perspective view of another configuration of the tube with a first wire and a second wire extending from the end of the tube and being in physical contact with one another to make an electrical connection.

In a third configuration shown in FIG. 8, the first and second wires 24A, 24B extend from the end of the tube 12 and are electrically connected to one another by making physical contact, such as by being twisted together. The tube 12 may or may not include the temperature sensor 14.

Figure 9:
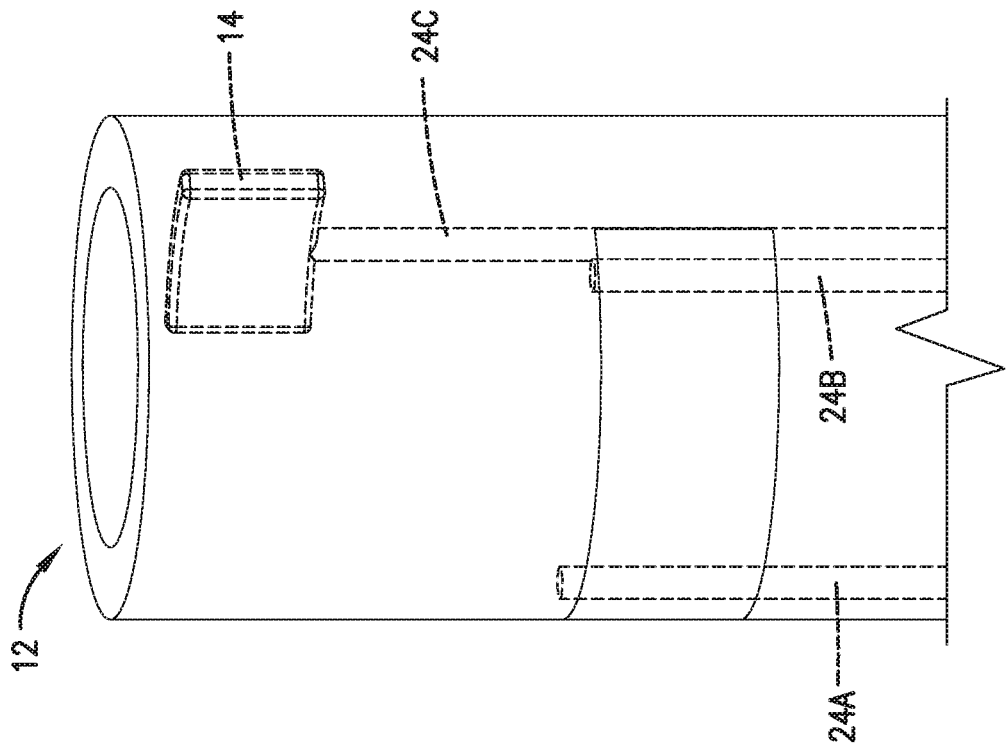
FIG. 9 is a perspective view of another configuration of the tube with an electrically conductive paste creating an electrical connection between two of the wires within the tube and the paste being covered by an electrical insulator.
Figure 10:
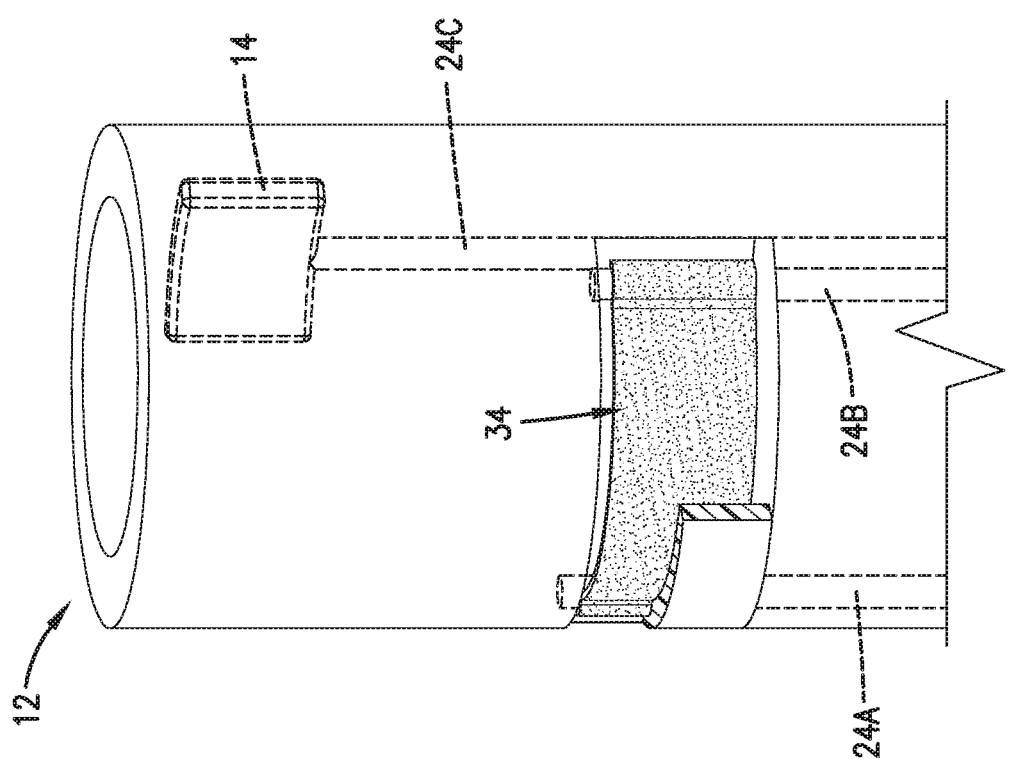
FIG. 10 is a perspective view of the configuration of FIG. 9 with a portion of the insulator removed to reveal the conductive paste underneath.

In a fourth configuration shown in FIGS. 9 and 10, the tube 12 includes the first and second wires 24A, 24B which are electrically connected to one another with an electrically conductive paste 34. To form the connection, a portion of the side wall 22 along the outer surface of the tube 12 between the ends of the first and second wires 24A, 24B may be removed which forms a trench. The conductive paste 34 may be injected in, or applied to, the trench between the first and second wires 24A, 24B to form an electrical connection. The conductive paste 34 may then be covered over by an insulating material, such as Kapton tape or the like. The tube 12 includes the third wire 24C electrically connected to the temperature sensor 14, which is positioned near the first end. Alternatively, the tube 12 may not include the temperature sensor 14 and/or the third wire 24.

The connector 16 generally couples the first end of the tube 12 to a line connector 30 and line tubing 32 for the IV line 20 that connects to a patient's body. The connector 16 includes a first side wall 36, a second side wall 38, a third side wall 40, and a base 42. The first side wall 36 has a hollow generally cylindrical shape presenting an inner surface and an outer surface and includes a first end and an opposing second end. The first end of the first side wall 36 (also considered the first end of the connector 16) is configured to be coupled with the first end of the tube 12, such that the first end of the tube 12 is retained inside the first side wall 36 and an outer surface of the tube 12 contacts an inner surface of the first side wall 36. Thus, an inner diameter of the first end of the first side wall 36 is slightly greater than an outer diameter of the tube 12. In addition, the first side wall 36 may have a beveled interior edge at the first end thereof. The second end of the first side wall 36 couples to the base 42.

The second side wall 38 has a hollow generally cylindrical shape presenting an inner surface and an outer surface and includes a first end and an opposing second end. The first end of the second side wall 38 is configured to be coupled with the line tubing 32, while the second end is coupled to the base 42. An outer diameter of the first end of the second side wall 38 is slightly less than an inner diameter of the line tubing 32 so that the line tubing 32 fits over the second side wall 38 of the connector 16 when the line tubing 32 is coupled to the connector 16.

In certain embodiments, the first side wall 36 and the second side wall 38 may be, or may be considered, a single side wall with a first end (the first side wall 36) and a second end (the second side wall 38).

The third side wall 40 has a hollow generally cylindrical shape presenting an inner surface and an outer surface and includes a first end and an opposing second end. The third side wall 40 has an inner diameter that is greater than the outer diameter of the second side wall 38 so that the third side wall 40 is spaced apart from, and positioned concentrically to, the second side wall 38. The first end of the third side wall 40 is configured to receive the line connector 30 for the IV line tubing 32 while the second end is coupled to the base 42. The third side wall 40 further includes internal threading along its inner surface that is configured to mate with external threading along an outer surface of the line connector 30.

The base 42 has a generally annular or disc shape with a first surface and an opposing second surface, an inner edge and an opposing outer edge. The second side wall 38 is coupled to the first surface at the inner edge while the third side wall 40 is coupled to the first surface at the outer edge. The first side wall 36 is coupled to the second surface in between the inner edge and the outer edge.

In some embodiments, the connector 16 is formed from plastics, polymers, or the like which may be transparent or partially transparent. In other embodiments, the connector 16, in its entirety or at least in part, is formed from electrically conductive material. For example, all of the connector 16 may be formed from a metal or metal alloy. Or, just a portion, such as the first side wall 36, may be formed from a metal or metal alloy, while the remainder is formed from another material such as a polymer. In other examples, the material of the connector 16 may be doped with, infused with, mixed with, or combined with, electrically conductive particles, such as nano metal particles, so that at least part of the connector 16, such as the first side wall 36, is capable of carrying electric current and/or is capable of forming an electrical connection. In still other examples, the connector 16, in its entirety or at least in part, is formed from an injection-molded thermoplastic material that is doped with a non-electrically-conductive metallic inorganic compound. In a process known as laser direct structuring, a laser may then be applied to the surfaces where electrical conductivity is desired, such as the surfaces of the first side wall 36. This activates the metal to become electrically conductive. Additional layers of metal may also be added on top of the activated metal through processes such as plating. Thus, at least part of the connector 16, such as the first side wall 36, is capable of carrying electric current and/or is capable of forming an electrical connection.

In some embodiments shown in FIG. 11, instead of the temperature sensor 14 being retained in the tube 12, the connector 16 retains the temperature sensor 14 within the first side wall 36. The temperature sensor 14 may be a wireless temperature sensor 14 that communicates temperature data wirelessly. Alternatively, the temperature sensor 14 may communicate temperature data or a temperature signal through a wire. In such a situation, at least a portion of the temperature sensor 14 may be exposed to the inner surface of the first side wall 36. On the tube 12, the third wire 24C may extend through, or be exposed on, the first end of the side wall 22 of the tube 12, such that when the tube 12 is coupled with the connector 16, the third wire 24C makes electrical contact with the temperature sensor 14.

In some embodiments shown in FIGS. 12 and 13, the connector 16 further includes a plurality of jumpers 44 retained by the first side wall 36. Each jumper 44 is formed from electrically conductive material, such as metals or metal alloys, and is generally elongated with a first end that is embedded in the first side wall 36 and a second end extending from the first side wall 36 and projecting radially inward to the axial center of the connector 16. In various embodiments, each jumper 44 may have a sharp edge, like a barb, to pierce the side wall 22 of the tube 12 and make electrical contact with one of the wires 24. Additionally, or alternatively, the tube 12 may include a plurality of cutouts, or detents, along the edge of the tube 12—including one cutout for each wire 24 that exposes the wire 24 and makes alignment of the wires 24 and the jumpers 44 easier. In addition, between two of the jumpers 44 is a bridge 46 formed from electrically conductive material and embedded in the first side wall 36 of the connector 16. The bridge 46 forms an electrical connection between the jumpers 44 so that the first wire 24A and the second wire 24B are electrically connected when the tube 12 is inserted into the connector 16, as shown in FIG. 13. Furthermore, one of the jumpers 44 may be electrically connected to the temperature sensor 14, which, for the embodiments of FIGS. 12 and 13, is embedded in the first side wall 36 of the connector 16.

In some embodiments shown in FIGS. 14 and 15, the connector 16 further includes a ring 48 retained by the first side wall 36. The ring 48 is formed from electrically conductive material, such as metals or metal alloys, and has a generally circular shape with a single side wall having an inner surface that is exposed to the interior of the first side wall 36 of the connector 16. The ring 48 forms an electrical connection between the first wire 24A and the second wire 24B of the tube 12 when the tube 12 is inserted in the connector 16, as shown in FIG. 15.

Referring at least in part to FIG. 3, the tube and connector assembly 10 may be utilized as follows. The connector 16 is coupled with the tube 12 typically by inserting the first end of the tube 12 into the first end of the first side wall 36 of the connector 16. The connector 16 may then be pushed onto the tube 12. The line connector 30 may be coupled with the connector 16 of the assembly 10, typically by screwing the line connector 30 into the connector 16. Assuming that the fluid bag connector 26 is coupled to the fluid bag 18 and the thermal controller and power supply 28, then the fluid from the fluid bag 18 may flow through the tube 12. The temperature sensor 14 measures the temperature of the tube 12 and, by extension, the fluid flowing within. The temperature sensor 14 communicates temperature data or the temperature signal to the thermal controller and power supply 28. If the measured temperature is sufficiently different from a set, or desired, temperature, then the thermal controller and power supply 28 may adjust the electric voltage and/or electric current to the first and second wires 24A, 24B in order to adjust the temperature to within a range of the set temperature.

The temperature sensor 14 is positioned either within the tube 12 near the first end thereof, or in the connector 16. This positioning allows the tube and connector assembly 10 to monitor and adjust the temperature of the fluid just before it exits the assembly 10—providing fluid temperature control at a point close to where the fluid enters the patient's body.

In another configuration shown in FIG. 16, the tube and connector assembly 10 may include a sleeve 50. The sleeve 50 may be formed from thermally-adjustable polymers, such as heat-shrink tubing, resilient materials, such as latex, or other materials that can be crimped onto the tube and connector assembly 10. The tube 12 may be inserted or positioned in the first side wall 36 of the connector 16. The sleeve 50 may then be placed over the joint of the tube 12 and the connector 16. If appropriate, heat may be applied to the sleeve 50 to shrink the sleeve 50 such that it fits tightly over the joint of the tube 12 and the connector 16. Specifically, the sleeve 50 may cover a portion of the tube 12 and a portion of the first side wall 36.

In yet another configuration shown in FIG. 17, the tube 12 may be coupled to the connector 16 such that the tube 12 fits over the first side wall 36 of the connector 16 and an inner surface of the tube 12 contacts an outer surface of the first side wall 36. The sleeve 50 may be placed over the joint of the tube 12 and the connector 16. If appropriate, heat may be applied to the sleeve 50.

A second embodiment of the tube and connector assembly 100 is shown in FIGS. 18-20. A second embodiment of the tube 112 is shown in FIG. 18 and is substantially similar to the tube 12 except that the first end includes external threads on the outer surface of the side wall 22. In addition, the first end of the tube 112, where the threads are located, may have a larger outer diameter than the outer diameter of the tube 12.

A second embodiment of the connector 116 is shown in FIGS. 19 and 20. The connector 116 includes a first side wall 136, a second side wall 138, a third side wall 140, and a base 142. The first side wall 136 has a hollow generally cylindrical shape presenting an inner surface and an outer surface and includes a first end and an opposing second end. The outer surface may taper inward from an approximate axial midpoint to each of the first end and the second end, such that the first side wall 136 has a thickness that is greater at the axial midpoint than at each of the first end and the second end.

The second side wall 138 has a hollow generally cylindrical shape presenting an inner surface and an outer surface and includes a first end and an opposing second end. The second side wall 138 has an inner diameter that is greater than the outer diameter of the first side wall 136 so that the second side wall 138 is spaced apart from, and positioned concentrically to, a first half of the first side wall 136. The second side wall 138 further includes internal threading along its inner surface. The second end of the second side wall 138 is coupled to the base 142.

The third side wall 140 has substantially the same structure as the second side wall 138 and is inverted from the second side wall 138 such that the second end of the third side wall 140 couples to the base 142 opposite from the second end of the second side wall 138. In some embodiments, the third side wall 140 and the second side wall 138 may be considered to be a single monolithic side wall. The third side wall 140 is spaced apart from, and positioned concentrically to, a second half of the first side wall 136. In addition, the third side wall 140 further includes internal threading along its inner surface.

The base 142 has a generally annular or disc shape with a first surface and an opposing second surface, an inner edge and an opposing outer edge. The inner edge is coupled to an approximate axial midpoint of the outer surface of the first side wall 136, while the outer edge is coupled to the second side wall 138 and the third side wall 140.

In some embodiments, the connector 116 is formed from plastics, polymers, or the like which may be transparent or partially transparent. In other embodiments, the connector 116, in its entirety or at least in part, is formed from electrically conductive material. For example, all of the connector 116 may be formed from a metal or metal alloy. Or, just a portion, such as the first side wall 136 and/or the second side wall 138, may be formed from a metal or metal alloy, while the remainder is formed from another material such as a polymer. In other examples, the material of the connector 116 may be doped with, infused with, mixed with, or combined with, electrically conductive particles, such as nano metal particles, so that at least part of the connector 116, such as the first side wall 136 and/or the second side wall 138, is capable of carrying electric current and/or is capable of forming an electrical connection. In still other examples, the connector 116, in its entirety or at least in part, is formed from an injection-molded thermoplastic material that is doped with a non-electrically-conductive metallic inorganic compound. In a process known as laser direct structuring, a laser may then be applied to the surfaces where electrical conductivity is desired, such as the surfaces of the first side wall 136 and/or the second side wall 138. This activates the metal to become electrically conductive. Additional layers of metal may also be added on top of the activated metal through processes such as plating. Thus, at least part of the connector 116, such as the first side wall 136 and/or the second side wall 138, is capable of carrying electric current and/or is capable of forming an electrical connection.

The connector 116 is configured to couple or connect with the tube 112 such that the external threads of the tube 112 mate with and screw into the internal threads of the second side wall 138 of the connector 116, as best shown in FIG. 20.

In various embodiments, the connector 116 may also include the temperature sensor 14, the jumpers 44 and the bridge 46, or the ring 48. FIG. 21 illustrates the connector 116 with the temperature sensor 14 retained within the first side wall 136. The temperature sensor 14 may be wireless or may be wired.

FIG. 22 illustrates the connector 116 with the temperature sensor 14 and the jumpers 44 and the bridge 46 retained by the first side wall 136. With the connector 116, the jumpers 44 extend outward from an outer surface of the first side wall 136.

FIG. 23 illustrates the connector 116 with the electrically conductive ring 48 retained by the first side wall 136 such that a surface of the ring 48 is exposed to the exterior of the first side wall 136.

FIG. 24 illustrates the connector 116 with an electrically conductive material 150 mixed, or embedded, in the internal threads of the second side wall 138. Alternatively, or additionally, the connector 116 may include an electrically conductive coating or wiring 150 applied to, or positioned on, a surface of the internal threads of the second side wall 138. With any of the foregoing implementations, the internal threads provide an electrical connection between the first and second wires 24A, 24B of the tube 12 when the tube 12 is coupled to the connector 116.

Various additional embodiments of the current invention provide the connector 16, 116 as a standalone component. The connector 16, 116 may include any of the features or components discussed above, such as the temperature sensor 14, the jumpers 44 and the bridge 46, and the ring 48, either alone or in various combinations.

ADDITIONAL CONSIDERATIONS

Throughout this specification, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current invention can include a variety of combinations and/or integrations of the embodiments described herein.

Although the present application sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

The patent claims at the end of this patent application are not intended to be construed under 35 U.S.C. § 112(f) unless traditional means-plus-function language is expressly recited, such as "means for" or "step for" language being explicitly recited in the claim(s).

Although the technology has been described with reference to the embodiments illustrated in the attached drawing figures, it is noted that equivalents may be employed and substitutions made herein without departing from the scope of the technology as recited in the claims.

The invention claimed is:

1. A connector for use with intravenous fluid tubes, the connector comprising:
   a first hollow generally cylindrical side wall including an outer surface and an opposing inner surface, the first hollow generally cylindrical side wall configured to receive a first tube contacting the inner surface and supplying intravenous fluid from a fluid bag, the first tube including an outer surface which contacts the inner surface of the first hollow generally cylindrical side wall;
   a second hollow generally cylindrical side wall positioned opposite the first side wall and configured to receive a second tube from an intravenous line;
   a third hollow generally cylindrical side wall spaced apart from and concentric with the second side wall, the third side wall including threads on an inner surface thereof and configured to receive a line connector for the intravenous line; and
   a temperature sensor positioned within the first side wall so as not to penetrate the inner surface of the first side wall and configured to measure a temperature of the intravenous fluid flowing through the connector.

2. The connector of claim 1, further comprising a first jumper and a second jumper retained by the first side wall, the first and second jumpers electrically connected to one another, the first jumper configured to electrically connect to a first wire of the first tube and the second jumper configured to electrically connect to a second wire of the first tube when the first tube is coupled to the connector.

3. The connector of claim 1, wherein at least a portion of the connector is formed from electrically conductive material.

4. The connector of claim 2, further comprising a third jumper retained by the first side wall, the third jumper electrically connected to the temperature sensor and configured to electrically connect to a third wire of the first tube when the first tube is coupled to the connector.

5. A connector for use with intravenous fluid tubes, the connector comprising:
   a first hollow generally cylindrical side wall including an outer surface and an opposing inner surface, the first hollow generally cylindrical side wall configured to receive a first tube supplying intravenous fluid from a fluid bag, the first tube including an outer surface which contacts the inner surface of the first hollow generally cylindrical side wall;
   a second hollow generally cylindrical side wall positioned opposite the first side wall and configured to receive a second tube from an intravenous line;
   a third hollow generally cylindrical side wall spaced apart from and concentric with the second side wall, the third side wall including threads on an inner surface thereof and configured to receive a line connector for the intravenous line; and
   a first jumper and a second jumper retained by the first side wall and spaced apart from one another along the circumference of the first side wall, the first and second jumpers electrically connected to one another, each of the first jumper and the second jumper including a first end that is embedded in the first side wall and a second end extending from the first side wall and projecting radially inward, the first jumper configured to electrically connect to a first wire of the first tube and the second jumper configured to electrically connect to a second wire of the first tube when the first tube is coupled to the connector.

\* \* \* \* \*